(12) United States Patent
Garbaccio et al.

(10) Patent No.: US 8,329,697 B2
(45) Date of Patent: Dec. 11, 2012

(54) IMIDIZO[1,2-A]PYRAZINES USEFUL AS AHCY HYDROLASE INHIBITORS

(75) Inventors: Robert M. Garbaccio, Lansdale, PA (US); Antonella Converso, Elkins Park, PA (US); Mark E. Fraley, North Wales, PA (US); Timothy J. Hartingh, Blue Bell, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 163 days.

(21) Appl. No.: 12/811,911

(22) PCT Filed: Feb. 18, 2009

(86) PCT No.: PCT/US2009/034344
§ 371 (c)(1),
(2), (4) Date: Jul. 7, 2010

(87) PCT Pub. No.: WO2009/108546
PCT Pub. Date: Sep. 3, 2009

(65) Prior Publication Data
US 2010/0305135 A1    Dec. 2, 2010

Related U.S. Application Data

(60) Provisional application No. 61/067,210, filed on Feb. 26, 2008.

(51) Int. Cl.
*A61K 31/495*    (2006.01)
(52) U.S. Cl. .................................. 514/249; 544/350
(58) Field of Classification Search .................. 514/249; 544/350
See application file for complete search history.

(56) References Cited

U.S. PATENT DOCUMENTS

| 4,507,294 A | 3/1985 | Bristol et al. |
| 5,521,162 A | 5/1996 | Jarvi et al. |
| 7,208,495 B2 | 4/2007 | Ohkawa et al. |
| 2004/0204429 A1 | 10/2004 | Yuan |

FOREIGN PATENT DOCUMENTS

WO    WO 2009/108546    *    9/2009

OTHER PUBLICATIONS

Jordan, V. C. Nature Reviews: Drug Discovery, 2, 2003, 205.*
Hackam, et al. JAMA, 296(14), 2006, 1731-1732.*

* cited by examiner

*Primary Examiner* — Douglas M Willis
(74) *Attorney, Agent, or Firm* — Kenrick L. Vidale; John C. Todaro

(57) ABSTRACT

The present invention is directed to AHCY inhibitors of formula (I) which are useful in the treatment of diseases characterized by high homocysteine levels, such as Alzheimer's disease. The invention is also directed to pharmaceutical compositions comprising the compounds, and to the use of the compounds and compositions in the treatment of diseases characterized by high homocysteine levels.

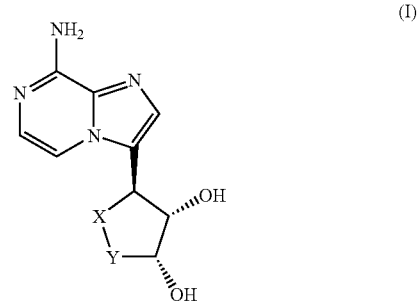

(I)

7 Claims, No Drawings

IMIDIZO[1,2-A]PYRAZINES USEFUL AS AHCY HYDROLASE INHIBITORS

CROSS-REFERENCE TO RELATED APPLICATIONS

This application claims the benefit under 35 U.S.C. 119(e) of U.S. Provisional Application No. 61/067,210, filed 26 Feb. 2008.

BACKGROUND OF THE INVENTION

1. Field of the Invention

The invention is directed to a class of S-adenosyl homocysteine hydrolase (AHCY) inhibitors, their salts, pharmaceutical compositions comprising them and their use in therapy of the human body. In particular, the invention is directed to a class of AHCY inhibitors, which are useful in the treatment of diseases characterized by high homocysteine levels.

2. Description of Related Art

S-adenosylhomocysteine, known as AdoHcy, is an intermediate in the metabolism of the sulfur-containing amino acids methionine and cysteine. AdoHcy is formed by the donation of a methyl group from S-adenosylmethionine (SAM) to biomolecules undergoing methylation reactions. AdoHcy is then metabolized by the enzyme S-adenosylhomocysteine hydrolase, known as AHCY, SAHH or SAH hydrolase, which reversibly hydrolyses AdoHcy to adenosine and homocysteine. Homocysteine can be remethylated back to methionine or undergo a series of metabolic steps leading to the biosynthesis of glutathione or cysteine. Following the hydrolysis of AdoHcy, homocysteine can also be secreted from the body or converted into the anti-oxidant, glutathione, by a series of transulfuration pathway reactions. Glutathione is a major anti-oxidant in the body. The relative ratio between oxidized and reduced forms of glutathione is thought to be an important indicator of oxidative state.

Furthermore, the ratio between SAM and AdoHcy is critical for many biological processes, as AdoHcy can inhibit many methyltransferases that use SAM as a methyl donor. Thus, the rate of conversion of AdoHcy to Hcy is a critical regulator of many biological reactions involving phospholipids, proteins, and nucleic acids. Chiang, *Pharmacol Ther* 1998, 77, 2, 115-134. Various nucleosides and nucleoside derivatives act as inhibitors of AHCY. Chiang.

Homocysteine metabolism is also dependent on the nutrients folate, vitamin B12 and vitamin B6. Obeid et al, *FEBS Letters* 2006, 580:2994-3005. These nutrients are cofactors for the enzymes that remethylate Hcy back to methionine (folate, B12) or convert it to glutathione (B6).

AHCY is a 432 amino acid protein, which is a thioether hydrolase. AHCY is a cytosolic enzyme that has been found in a wide variety of cells. Walker, et al. *Can. J. Biochem.* 1975 53: 312-319. The sequence of AHCY is disclosed in International Patent Application Publication No. WO 2005/015221.

AHCY catalyzes the conversion of S-adenosyl-homocysteine to homocysteine and adenosine. Because of the key role of AdoHcy in the synthesis of cysteine, and the role of S-adenosylmethionine as a universal methyl donor, misregulation of AHCY can affect methylation of phosphlipids, proteins, DNA and RNA.

Epidemiological evidence demonstrates that increased levels of homocysteine are associated with many diseases, including cardiovascular disease, stroke, and neurodegenerative diseases such as Alzheimer's Disease. Hyperhomocysteinemia, which may be caused by folic acid deficiency, can contribute to Alzheimer's Disease. Morris, *Lancet Neurol.* 2003 2(7):425-8. Further, the known AHCY inhibitor 3-deaza-adenosine (DZA) has been shown to prevent oxidative damage and cognitive impairment in mice. Shea et al, *Neuromolecular Medicine* 2004, 5:173-182. In clinical studies, folate deficiency was associated with neurological disorders such as Alzheimer's disease. Ho et al., *Neurobiology of Disease,* 2003 14: 1, 32-42.

Seshadri et al, *N Engl. J. Med,* 2002, 346:476-483, in a study of data from the Framingham Heart Study, found that increased homocysteine levels in plasma was an independent risk factor for dementia and Alzheimer's Disease. See also Morris, *Lancet Neurology* 2003, 2:425-428.

Hyperhomocysteinemia is a known risk factor for arterial vascular disease and venous thrombosis. Gellekink et al, *Eur J Hum Genet.* 2004 12(11):942-8; cardiovascular disease, Levine et al, *Prog Neuropsych Biol Psych* 2005, 29(7):1181-91; schizophrenia, Haidemenos et al, *Prog Neuropsychopharmacol Biol Psychiatry.* 2007 15; 31(6):1289-96; and bipolar disorder, Levine et al. Elevated homoscysteine levels have also been shown to be risk factors for stroke and Parkinson's Disease. Herrmann et al, *Fortschr Neurol Psychiatr.* 2007 75(9):515-27. Further, animal studies suggest that increased homocycsteine levels may be a factor in osteoporosis. Herrmann et al, *Clin. Chem.* 2007, 53(8):1455-61.

One possible method for treating diseases via the AHCY pathway is to develop mechanisms for clearing homocysteine from the body. For example, compounds or substances that increase the rate of vitamin B clearance of homocysteine in vivo may find utility as agents for treating disease associated with high levels of homocysteine. A second method of interfering with the AHCY pathway is to decrease production of homocytseine, i.e. to develop compounds that can inhibit production of homocysteine in vivo. For example, compounds or substances which inhibit AHCY may decrease the extent of hydrolysis of S-adenosyl homocysteine into homocysteine and adenosine.

The inventors have identified a novel group of compounds which act as inhibitors of S-adenosyl homocysteine hydrolase, thereby inhibiting the hydrolysis of S-adenosyl homocysteine into homocysteine and adenosine.

BRIEF SUMMARY OF THE INVENTION

The present invention is directed to novel compounds of generic formula (I)

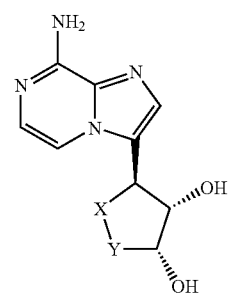

or pharmaceutically acceptable salts thereof, which are useful as AHCY inhibitors.

The invention is further directed to methods of treating a patient (preferably a human) for diseases or disorders which are characterized by high homocysteine levels, such as Alzheimer's disease, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to compounds of general formula (I)

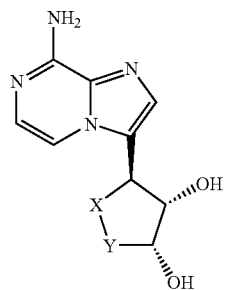

and pharmaceutically acceptable salts thereof, wherein
X—Y is selected from the group consisting of
(1) $CH_2$—$CR^1R^2$,
(2) $CH$=$CR^1$;
$R^1$ is selected from the group consisting of
(1) hydrogen,
(2) hydroxyl,
(3) —$C_{1-6}$ alkyl, wherein said alkyl is optionally substituted with
(a) halogen, or
(b) hydroxyl; and
$R^2$ is selected from the group consisting of
(1) hydrogen,
(2) hydroxyl,
(3) —$C_{1-6}$ alkyl, wherein said alkyl is optionally substituted with
(a) halogen, or
(b) hydroxyl.
In one embodiment, $R^1$ is selected from the group consisting of
(1) hydrogen, and
(2) —$C_{1-3}$ alkyl, wherein said alkyl is optionally substituted with
(a) halogen, or
(b) hydroxyl.
In another embodiment, $R^1$ is selected from the group consisting of
(1) hydrogen, and
(2) —$CH_2OH$.
In one embodiment, the invention is directed to methods of treating a patient (preferably a human) for diseases characterized by high homocysteine levels, such as Alzheimer's Disease, hypertension, cardiovascular disease, stroke and schizophrenia, by administering to the patient a therapeutically effective amount of a compound of general formula (I).
The invention is also directed to the use of a compound of formula (I) for treating diseases or disorders characterized by high homocysteine levels, such as Alzheimer's disease, hypertension, cardiovascular disease, stroke and schizophrenia.

The invention is also directed to medicaments or pharmaceutical compositions for treating diseases or disorders characterized by high homocysteine levels, such as Alzheimer's disease, hypertension, cardiovascular disease, stroke and schizophrenia, which comprise a compound of formula (I), or a pharmaceutically acceptable salt thereof, and a pharmaceutically acceptable carrier.

The invention is further directed to a method for the manufacture of a medicament or a composition for treating diseases or disorders characterized by high homocysteine levels, such as Alzheimer's disease, hypertension, cardiovascular disease, stroke or schizophrenia, comprising combining a compound of formula (I) with one or more pharmaceutically acceptable carriers.

Specific embodiments of formula (I) are described herein as Examples 1 ((1S,2R,5S)-5-(8-aminoimidazo[1,2-a]pyrazin-3-yl)-3-(hydroxymethyl)cyclopent-3-ene-1,2-diol) and 2 (1R,2S,3S)-3-(8-aminoimidazo[1,2-a]pyrazin-3-yl)cyclopentane-1,2-diol, and pharmaceutically acceptable salts thereof.

Where a variable occurs more than once in Formula (I) or in a substituent thereof, the individual occurrences of that variable are independent of each other, unless otherwise specified.

As used herein, in particular in the definitions of $R^1$, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tent-butyl, pentyl, hexyl, and the like. $C_0$ alkyl means a bond.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formula (I).

Formula (I) is shown above without a definite stereochemistry at certain positions. The present invention includes all stereoisomers of formula (I) and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & Wuts, *Protective Groups in Organic Synthesis*, John Wiley & Sons, 1991. The protecting groups may be removed at a convenient sequent stage using methods known from the art.

The term "substantially pure" means that the isolated material is at least 90% pure, and preferably 95% pure, and even more preferably 99% pure as assayed by analytical techniques known in the art.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like.

The present invention is directed to the use of the compounds of formula (I) disclosed herein as AHCY hydrolase inhibitors in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases characterized by high homocysteine levels, such as Alzheimer's disease. Other conditions that may be treated by the compounds of the invention include Parkinson's Disease, hypertension, schizophrenia, including the positive and negative symptoms of schizophrenia and treatment of cognitive impairment due to schizophrenia, bipolar disorder, cancer, cardiovascular disease, viral infections and osteoporosis.

In certain embodiments, the compounds of the invention are useful in treating Alzheimer's Disease. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anaesthetics, amphetamine and other psychostimulants and cocaine), psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnesiac disorders or age related cognitive decline.

In one embodiment, the present invention provides a method for treating cognitive disorders, comprising: administering to a patient in need thereof an effective amount of a compound of the present invention. Particular cognitive disorders are dementia, delirium, aninestic disorders and age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

Potential cardiovascular conditions or disorders for which the compounds of the invention may be useful include atherosclerosis, hypertension, hyperlipidemia, coronary heart disease, peripheral vascular disease, dyslipidemia, hyperbetalipoproteinemia, hypoalphalipoproteinemia, hypercholesterolemia, hypertriglyceridemia, familial-hypercholesterolemia, angina, ischemia, cardiac ischemia, stroke, myocardial infarction, reperfusion injury, angioplastic restenosis, vascular complications of diabetes, obesity (including abdominal obesity) and endotoxemia.

The compounds of the invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease.

As stated above, the compounds of the invention may be used for treating stroke. One class of stroke patients to which a compound of the invention may be administered is a patient at risk for stroke. As used herein, the term "patient at risk for stroke" means an individual who has had a previous stroke, or has a risk factor for stroke. Known risk factors for stroke include atherosclerosis, arterial hypertension, lipohyalinosis, hyperlipidemia, hypercholesterolemia, atrial fibrillation, smoking, inflammatory markers (including C-reactive protein), infection, homocysteine, sleep-disordered breathing, cerebral autosomal dominant arteriopathy with subcortial infarcts and leuko-encephalopathy (CADASIL), migraine, sickle-cell anemia, antiphospholipid antibody syndrome, arterial dissection, cocaine abuse and obesity.

A second class of patients to which a compound of the invention may be administered are acute stroke patients, i.e., patients who have suffered ischemic stroke within the last 7 days. One class of acute stroke patients are those who have suffered stroke within the last 3 days. Another class of acute stroke patients are those who have suffered stroke within the last 48 hours, for example within the last 24 hours. As common in the art of treating stroke, patients may be classified according to the period of time when stroke occurred, So, for example, one class of acute stroke patients are those who have suffered stroke within the last 18 hours. Another class of acute stroke patients are those who have suffered stroke within the last 12 hours. Another class of acute stroke patients are those who have suffered stroke within the last 8 hours. Another class of acute stroke patients are those who have suffered stroke within the last 6 hours. Another class of acute stroke patients are those who have suffered stroke within the last 4 hours. Another class of acute stroke patients are those who have suffered stroke within the last 3 hours.

A third class of patients to which a compound of the present invention may be administered are patients who have suffered stroke more than 7 days previously, who are typically in need of restorative treatment.

The subject or patient to whom the compounds of the present invention is administered is generally a human being, male or female, characterized by high homocysteine, but may also encompass other mammals, such as dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists, such as ABT089, SSR180711 and MEM63908; ADAM 10 ligands or activators; gamma-secretase inhibitors, such as LY450139 and TAK 070; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists, such as PRX-03140; 5-HT6 antagonists, such as GSK 742467, SOS-518, FK-962, SL-65.0155, SRA-333 and xaliproden; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab, ACC001, CAD106, AZD3102, H12A11V1; anti-inflammatory compounds such as (R)-flurbiprofen, nitroflurbiprofen, ND-1251, VP-025, HT-0712 and EHT-202; PPAR gamma agonists, such as pioglitazone and rosiglitazone; CB-1 receptor antagonists or CB-1 receptor inverse agonists, such as AVE1625; antibiotics such as doxycycline and rifampin; N-methyl-D-aspartate (NMDA) receptor antagonists, such as memantine, neramexane and EVT101; cholinesterase inhibitors such as galantamine, rivastigmine, donepezil, tacrine, phenserine, ladostigil and ABT-089; growth hormone secretagogues such as ibutamoren, ibutamoren mesylate, and capromorelin; histamine $H_3$ receptor antagonists such as ABT-834, ABT 829, GSK 189254 and CEP16795; AMPA agonists or AMPA modulators, such as CX-717, LY 451395, LY404187 and S-18986; PDE IV inhibitors, including MEM1414, HT0712 and AVE8112; $GABA_A$ inverse agonists; GSK3β inhibitors, including AZD1080, SAR502250 and CEP16805; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of other active ingredients that may be administered in combination with a composition of the present invention, and either administered separately or in the same pharmaceutical composition, include agents for the treatment of diabetic conditions, such as (a) insulin sensitizers including (i) PPARγ agonists, such as the glitazones (e.g. troglitazone, pioglitazone, englitazone, MCC-555, rosiglitazone, balaglitazone, and the like) and other PPAR ligands, including PPARα/γ dual, agonists, such as KRP-297, muraglitazar, naveglitazar, tesaglitazar, and TAK-559; PPARα agonists, such as fenofibric acid derivatives (gemfibrozil, clofibrate, fenofibrate and bezafibrate); and selective PPARγ modulators (SPPARγM's), such as disclosed in WO 02/060388, WO 02/08188, WO 2004/019869, WO 2004/020409, WO 2004/020408, and WO 2004/066963; (ii) biguanides, such as metformin and phenformin, and (iii) protein tyrosine phosphatase-1B (PTP-1B) inhibitors;

(b) insulin or insulin mimetics;

(c) sulfonylureas and other insulin secretagogues, such as tolbutamide, glyburide, glipizide, glimepiride, and meglitinides, such as nateglinide and repaglinide;

(d) α-glucosidase inhibitors (such as acarbose and miglitol);

(e) glucagon receptor antagonists, such as those disclosed in WO 97/16442; WO 98/04528, WO 98/21957; WO 98/22108; WO 98/22109; WO 99/01423, WO 00/39088, and WO 00/69810; WO 2004/050039; and WO 2004/069158;

(f) GLP-1, GLP-1 analogues or mimetics, and GLP-1 receptor agonists, such as exendin-4 (exenatide), liraglutide (N,N-2211), CJC-1131, LY-307161, and those disclosed in WO 00/42026 and WO 00/59887;

(g) GIP and GIP mimetics, such as those disclosed in WO 00/58360, and GIP receptor agonists;

(h) PACAP, PACAP mimetics, and PACAP receptor agonists such as those disclosed in WO 01/23420;

(i) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists, such as fenofibric acid derivatives (gemfibrozil, clofibrate, fenofibrate and bezafibrate), (v) PPARα/γ dual agonists, such as naveglitazar and muraglitazar, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(j) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(k) anti-obesity compounds, such as fenfluramine, dexfenfluramine, phentermine, sibutramine, orlistat, neuropeptide Y1 or Y5 antagonists, β3 adrenergic receptor agonists, melanocortin-receptor agonists, in particular melanocortin-4 receptor agonists, ghrelin antagonists, bombesin receptor agonists (such as bombesin receptor subtype-3 agonists), a cannabinoid CB1 receptor antagonist/inverse agonist, 5-FIT (serotonin) inhibitors, and melanin-concentrating hormone (MCH) receptor antagonists;

(l) ileal bile acid transporter inhibitors;

(m) agents intended for use in inflammatory conditions such as aspirin, non-steroidal anti-inflammatory drugs (NSAIDs), glucocorticoids, azulfidine, and selective cyclooxygenase-2 (COX-2) inhibitors;

(n) antihypertensive agents, such as neutral endopeptidase inhibitors (e.g., thiorphan and phosphoramidon), aldosterone antagonists, renin inhibitors (e.g. enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)phenyl]-octanamid hemifumarate) SPP600, SPP630 and SPP635), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, and peripheral vasodilators (e.g. hydralazine);

(o) glucokinase activators (GKAs), such as those disclosed in WO 03/015774; WO 04/076420; and WO 04/081001;

(p) inhibitors of 11β-hydroxysteroid dehydrogenase Type 1, such as those disclosed in U.S. Pat. No. 6,730,690; WO 03/104207; and WO 04/058741;

(q) inhibitors of cholesteryl ester transfer protein (CETP), such as torcetrapib; and (r) inhibitors of fructose 1,6-bisphosphatase, such as those disclosed in U.S. Pat. Nos. 6,054,587; 6,110,903; 6,284,748; 6,399,782; and 6,489,476;

(s) dipeptidyl peptidase IV (DP-IV) inhibitors;

(t) PPARδ agonists such as those disclosed in WO97/28149; and (u) agents intended for use in inflammatory conditions such as aspirin, non-steroidal anti-inflammatory drugs, glucocorticoids, azulfidine, and cyclo-oxygenase 2 selective inhibitors, including etoricoxib and rofecoxib.

Examples of anti-hypertensive agents that can be used in combination with the compounds of the invention include angiotensin II receptor antagonists (for example losartan, candesartan, irbesartan, valsartan, telmisartan, and eprosartan, including all stereoisomers, pharmaceutically acceptable salts, hydrates, and crystalline forms thereof), ACE inhibitors (for example, alacepril, benazepril, captopril, ceronapril, cilazapril, delapril, enalapril, enalaprilat, fosinopril, imidapril, lisinopril, moveltipril, moexipril, perindopril, quinapril, ramipril, spirapril, temocapril, and trandolapril), neutral endopeptidase inhibitors (e.g., thiorphan and phosphoramidon), aldosterone antagonists, renin inhibitors (e.g. urea derivatives of di- and tri-peptides), endothelin receptors antagonists, vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazocin, prazocin or alpha methyldopa) central alpha adrenergic agonists, and peripheral vasodilators (e.g. hydralazine).

Examples of agents for treating schizophrenia that can be used in combination with the compounds of the invention include sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

Alternatively, the compounds of the invention may be used in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexol)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

The compounds of the invention may also be used in combination with phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. The subject compound may be used in combination with acetophenazine, alentemol, aripiprazole, amisuipride, benzhexol, bromocriptine, biperiden, chiorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Further, the compounds of the invention may be used in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRTs), corticotropin releasing factor (CRF) antagonists, a-adrenoreceptor antagonists, neurokinin-1 receptor antagonists, atypical anti-depressants, benzodiazepines, 5-HT1A agonists or antagonists, especially S-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chiorazepate, diazepam, halazepam, lorazepam, oxazepam and prazepam; buspirone, flesinoxan, gepirone and ipsapirone, and pharmaceutically acceptable salts thereof.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formula (I), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention may be prepared according to the following reaction schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

Certain of the starting materials are described in Gallos, J. K. et al, *J. Org. Chem.*; 2005; 70(17); 6884-6890, Choi, W. J., et al, *J. Org. Chem.*; 2004; 69(7); 2634-2636, and Moon, Won Jun Choi, et al, *Tetrahedron Asymmetry*, 13 (11), 1189-1193.

The following examples are provided to illustrate the invention and are not to be construed as limiting the scope of the invention in any manner.

General Scheme A

According to general scheme A, appropriately substituted and/or protected cyclopentyl alcohols A-1 can be acylated with methyl chloroformate to produce carbonates A-2. Here X—Y can be either saturated (as in X—Y) or unsaturated (as in X=Y) and substituted according to the above generic claims. Carbonates A-2 are then reacted with vinyl magnesium bromide in the presence of copper (I) cyanide to provide the vinyl derivates A-3. Regioselective epoxidation of the terminal vinyl group (for example—over an internal X=Y double bond) is achieved using dimethyl dioxirane at low temperature to produce epoxides A-4. Epoxides A-4 are then regioselectively reacted with ammonia under thermal conditions to give the amino alcohols A-5. Amino alcohols A-5 are coupled with 2,3-dichloropyrazine to produce amino pyrazines A-6. Moffat-Swern oxidation of the secondary alcohol in pyrazines A-6 yields the ketone A-7 that is subsequently cyclized in the presence of trifluoroacetic acid and trfluoroacetic anhydride buffered by the presence of pyridine. These conditions provide the heterocyclic imidazopyrazines A-8. Imidazopyrazines A-8 are then reacted with ammonia under thermal conditions to provide imidazopyrazines A-9. Subsequent deprotection may vary depending on the nature of the X—Y substitution, but acid hydrolysis is utilized to remove the ketal group to provide final compounds A-10.

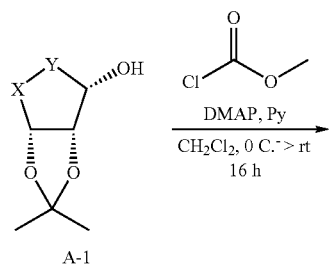

-continued
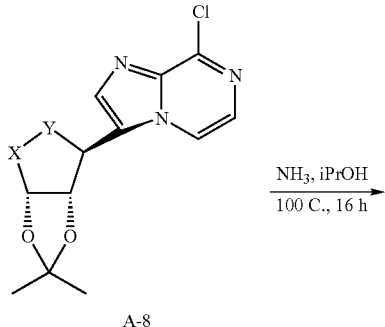
A-8
NH₃, iPrOH
———————
100 C., 16 h
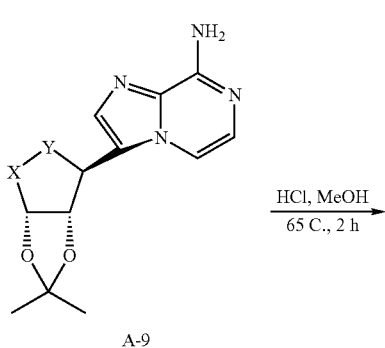
A-9
HCl, MeOH
———————
65 C., 2 h
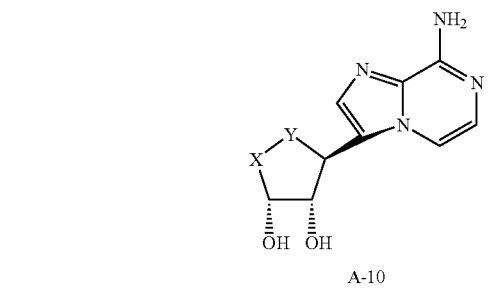
A-10
EXAMPLE 1
(1S,2R,5S)-5-(8-aminoimidazo[1,2-a]pyrazin-3-yl)-
3-(hydroxymethyl)cyclopent-3-ene-1,2-diol
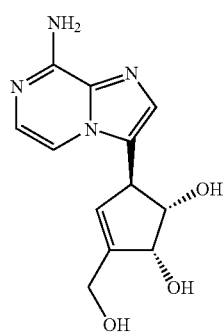
SYNTHETIC SCHEME
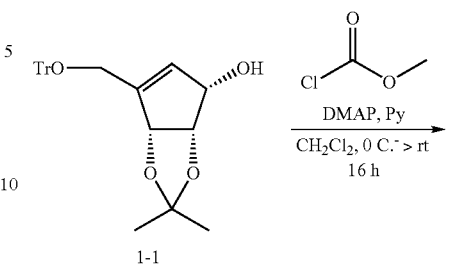
1-1
DMAP, Py
———————
CH₂Cl₂, 0 C. → rt
16 h
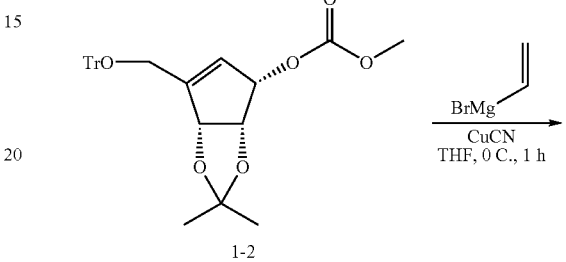
1-2
BrMg⁀
———————
CuCN
THF, 0 C., 1 h
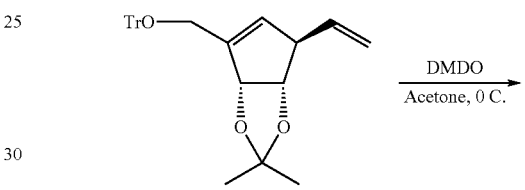
1-3
DMDO
———————
Acetone, 0 C.
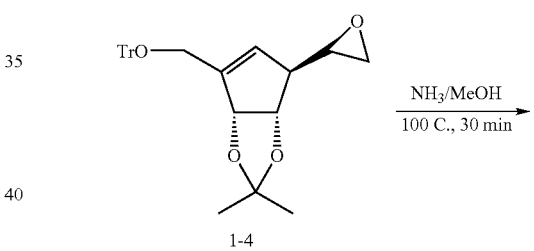
1-4
NH₃/MeOH
———————
100 C., 30 min
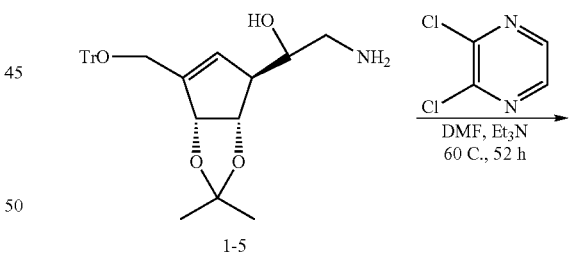
1-5
Cl, N, N, Cl
———————
DMF, Et₃N
60 C., 52 h
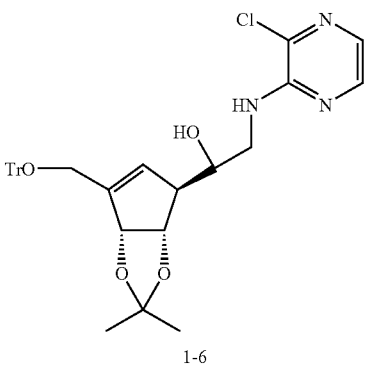
1-6
TFAA, DMSO
———————
DIPEA, CH₂Cl₂
−78 C., 2 h

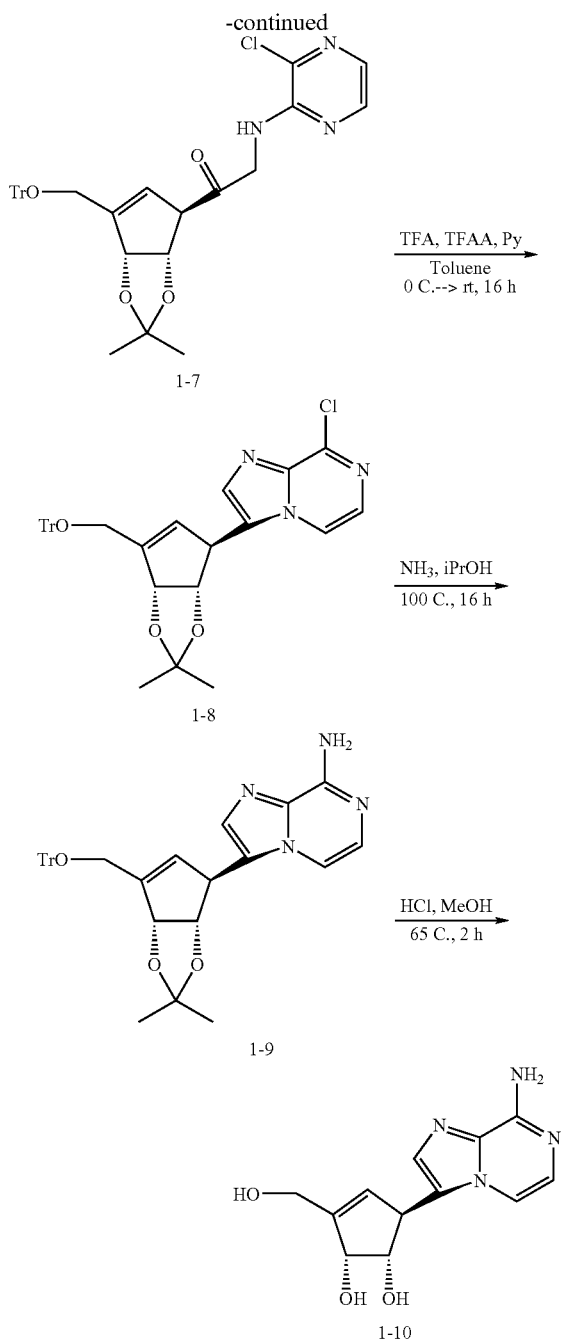

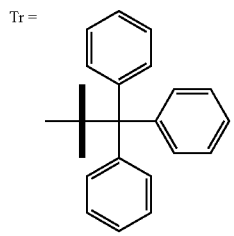

(3aS,4S,6aR)-2,2-dimethyl-6-(trityloxymethyl)-4,6a-dihydro-3aH-cyclopenta[d][1,3]dioxol-4-yl methyl carbonate (1-2)

(3aS,4S,6aR)-2,2-dimethyl-6-(trityloxymethyl)-4,6a-dihydro-3aH-cyclopenta[d][1,3]dioxol-4-ol (1-1) (1.44 g, 3.36 mmol, 1.0 equiv) as dissolved in DCM (11.2 mL). Pyridine (0.489 mL, 6.05 mmol, 1.8 equiv) was added and the mixture stirred at 0° C. After 1 hour DMAP (164 mg, 1.34 mmol, 0.4 equiv) was added followed by methyl chloroformate (1.04 mL, 13.44 mmol, 4 equiv). The resulting mixture was stirred 12 h, and the temperature was allowed to slowly increase to 23° C. The reaction was partitioned between DCM and water, and the organic layer was separated and washed with water, dried (MgSO$_4$), and concentrated to yield (3aS,4S,6aR)-2,2-dimethyl-6-(trityloxymethyl)-4,6a-dihydro-3aH-cyclopenta[d][1,3]dioxol-4-yl methyl carbonate (1-2) as a white foam. $^1$H NMR (00 MHz, CDCl$_3$) δ 7.21-7.47 (m, 15H), 6.03 (d, 1H, J=3.0 Hz), 5.32 (brm, 1H), 4.93 (t, 1H, J=9 Hz), 4.85 (d, 1H, J=10 Hz), 3.96 (d, 1H, J=24.5 Hz), 3.83 (s, 3H), 3.67 (d, 1H, J=24.5 Hz), 1.36 (s, 3H), 1.34 (s, 3H).

(3aS,4R,6aR)-2,2-dimethyl-6-(trityloxymethyl)-4-vinyl-4,6a-dihydro-3aH-cyclopenta[d][1,3]dioxole (1-3)

(3aS,4S,6aR)-2,2-dimethyl-6-(trityloxymethyl)-4,6a-dihydro-3aH-cyclopenta[d][1,3]dioxol-4-yl methyl carbonate (1-2) (1.2 g, 2.19 mmol, 1 equiv) was dissolved in anhydrous THF (22 mL) and cooled to 0° C. To the resulting mixture was added copper(I) cyanide (65 mg, 0.72 mmol, 0.33 equiv) followed by 0.7 M vinylmagnesium bromide solution in THF (7.84 mL, 5.49 mmol, 2.5 equiv). After 1 h at 0° C., the reaction was quenched with NH$_4$Cl (10 mL) and extracted with Et$_2$O (3×25 mL). The combined organic extracts were washed with water, dried (MgSO$_4$), and concentrated. Purification via flash chromatography on silica gel column (ethyl acetate/hexanes) gave (3aS,4R,6aR)-2,2-dimethyl-6-(trityloxymethyl)-4-vinyl-4,6a-dihydro-3aH-cyclopenta[d][1,3]dioxole (1-3). $^1$H NMR (500 MHz, CDCl$_3$) δ 7.25-7.55 (m, 15H), 5.94 (brd, 1H, J=0.5 Hz), 5.85 (ddd, 1H, J=7.5, 3, 17.5 Hz), 5.18 (dt, 1H, J=1.5, 17.5 Hz), 5.12 (dd, 1H, J=1, 10 Hz), 5.07 (d, 1H, J=5.5 Hz), 4.52 (d, 1H, J=6 Hz), 3.93 (d, 1H, J=14 Hz), 3.76 (d, 1H, J=14 Hz), 3.53 (d, 1H, J=7.5 Hz), 1.43 (s, 3H), 1.37 (s, 3H).

(3aS,4S,6aR)-2,2-dimethyl-4-((S)-oxiran-2-yl)-6-(trityloxymethyl)-4,6a-dihydro-3aH-cyclopenta[d][1,3]dioxole (1-4)

(3aS,4R,6aR)-2,2-dimethyl-6-(trityl oxymethyl)-4-vinyl-4,6a-dihydro-3aH-cyclopenta[d][1,3]dioxole (1-3) (1.4 g, 3.19 mmol, 1.0 equiv) was dissolved in a freshly prepared solution of DMDO (dimethyl dioxirane) in acetone (37.7 mL, 0.076 M, 0.9 equiv). The resulting mixture was stirred at 0° C. for 4 hours, then concentrated and purified via flash chromatography on silica gel column (ethyl acetate/hexanes) to yield (3aS,4S,6aR)-2,2-dimethyl-4-((S)-oxiran-2-yl)-6-(trityloxymethyl)-4,6a-dihydro-3aH-cyclopenta[d][1,3]dioxole (1-5). $^1$H NMR (500 MHz, CDCl$_3$) δ 7.21-7.47 (m, 15H), 5.83 (2 s, 1H), 4.99 (t, 1H, J=5 Hz), 4.63 (t, 1H, J=5 Hz), 3.86 (d, 1H, J=14 Hz), 3.67 (d, 1H, J=14 Hz), 2.85-2.97 (m, 2H), 2.77 (m, 1H), 2.60 (m, 1H), 1.35 (s, 3H), 1.32 (s, 3H).

(S)-2-amino-1-((3aS,4S,6aR)-2,2-dimethyl-6-(trityloxymethyl)-4,6a-dihydro-3aH-cyclopenta[d][1,3]dioxol-4-yl)ethanol (1-5)

(3aS,4S,6aR)-2,2-dimethyl-4-((S)-oxiran-2-yl)-6-(trityloxymethyl)-4,6a-dihydro-3aH-cyclopenta[d][1,3]dioxole (1-4) (2 g, 4.0 mmol, 1.0 equiv) was dissolved in a solution of ammonia in methanol (100 mL, 7 N). The mixture was heated in the microwave at 100° C. for 30 min. The reaction was concentrated to afford (S)-2-amino-1-((3aS,4S,6aR)-2,2-dimethyl-6-(trityloxymethyl)-4,6a-dihydro-3aH-cyclopenta[d][1,3]dioxol-4-yl)ethanol (1-5) as an amber solid that was carried to the next step without further purification. $^1$H NMR (500 MHz, CDCl$_3$) δ 7.21-7.45 (m, 15H), 5.81 (2 s, 1H), 5.00 (t, 1H, J=5 Hz), 4.57-4.70 (2 d, 1H, J=5.5 Hz), 3.77 (d, 1H, J=14 Hz), 3.66 (d, 1H, J=14 Hz), 3.31 (m, 1H), 2.57-2.88 (m, 2H), 1.30 (s, 3H), 1.29 (s, 3H). LRMS m/z (M+H) 472.1 found, 472.2 required.

(S)-2-(3-chloropyrazin-2-ylamino)-1-((3aS,4S,6aR)-2,2-dimethyl-6-(trityloxymethyl)-4,6a-dihydro-3aH-cyclopenta[d][1,3]dioxol-4-yl)ethanol (1-6)

(S)-2-amino-1-((3aS,4S,6aR)-2,2-dimethyl-6-(trityloxymethyl)-4,6a-dihydro-3aH-cyclopenta[d][1,3]dioxol-4-yl)ethanol (1-5) (2 g, 3.82 mmol, 1.0 eq) was dissolved in DMF (15.3 mL). 2,3-Dichloropyrazine (1.20 g, 7.63 mmol, 2 equiv) was added followed by triethylamine (2.13 mL, 15.3 mmol, 4 equiv). The reaction was stirred 20 hours at 60° C. Over a period of 52 hours 2,3-dichloropyrazine (299 mg, 1.91 mmol, 0.5 equiv) was added every 3 hours. The reaction was concentrated and purified via flash chromatography on silica gel column (ethyl acetate/hexanes) to yield (S)-2-(3-chloropyrazin-2-ylamino)-1-((3aS,6aR)-2,2-dimethyl-6-(trityloxymethyl)-4,6a-dihydro-3aH-cyclopenta[d][1,3]dioxol-4-yl)ethanol (1-6) as a white foam. $^1$H NMR (500 MHz, CDCl$_3$) δ 7.91 (d, 1H, J=1.5 Hz), 7.62 (d, 1H, J=1.5 Hz), 7.21-7.48 (m, 15H), 5.84 (2 s, 1H), 5.62 (m, 1H), 4.97 (t, 1H, J=6 Hz), 4.60-4.77 (2 d, 1H, J=7 Hz), 3.95 (d, 1H, J=14 Hz), 3.75 (m, 2H), 3.31 (m, 1H), 2.57-2.88 (m, 2H), 1.36 (s, 3H), 1.32 (s, 3H).

2-(3-chloropyrazin-2-ylamino)-1-((3aS,4R,6aR)-2,2-dimethyl-6-(trityloxymethyl)-4,6a-dihydro-3aH-cyclopenta[d][1,3]dioxol-4-yl)ethanone (1-7)

TFAA (0.459 mL, 3.25 mmol, 3.2 equiv) in DCM (0.5 mL) was added dropwise to DMSO (0.303 mL, 4.26 mmol, 4.2 equiv) in DCM (0.5 mL) at −78° C. After 30 minutes, (S)-2-(3-chloropyrazin-2-ylamino)-1-((3aS,4S,6aR)-2,2-dimethyl-6-(trityloxymethyl)-4,6a-dihydro-3aH-cyclopenta[d][1,3]dioxol-4-yl)ethanol (1-6) (593 mg, 1.01 mmol, 1 equiv) in DCM (2.7 mL) was added dropwise. The resulting mixture was stirred at −78° C. for 1 hour, at which point Hunig's base (1.06 mL, 6.09 mmol, 6 equiv) was added. After 30 minutes, the reaction was partitioned between sodium bicarbonate and DCM, and the aqueous phase was extracted with DCM (3×20 mL), the combined organic extracts were washed with water, dried (MgSO$_4$), and concentrated. The resulting yellow residue was purified via flash chromatography on silica gel column (ethyl acetate/hexanes) to yield 2-(3-chloropyrazin-2-ylamino)-1-((3aS,4R,6aR)-2,2-dimethyl-6-(trityloxymethyl)-4,6a-dihydro-3aH-cyclopenta[d][1,3]dioxol-4-yl)ethanone (1-7) as a colorless oil. $^1$H NMR (500 MHz, CDCl$_3$) δ 7.93 (d, 1H, J=3 Hz), 7.64 (d, 1H, J=3 Hz), 7.21-7.49 (m, 15H), 5.94 (s, 1H), 5.62 (m, 1H), 4.97 (t, 1H, J=6 Hz), 4.60-4.77 (2 d, 1H, J=7 Hz), 3.95 (d, 1H, J=14 Hz), 3.75 (m, 2H), 3.31 (m, 1H), 1.36 (s, 3H), 1.33 (s, 3H).

8-chloro-3-((3aS,4S,6aR)-2,2-dimethyl-6-(trityloxymethyl)-4,6a-dihydro-3aH-cyclopenta[d][1,3]dioxol-4-yl)imidazo[1,2-a]pyrazine (1-8)

2-(3-chloropyrazin-2-ylamino)-1-((3aS,4R,6aR)-2,2-dimethyl-6-(trityloxymethyl)-4,6a-dihydro-3aH-cyclopenta[d][1,3]dioxol-4-yl)ethanone (1-7) (401 mg, 0.69 mmol, 1 equiv) was dissolved in toluene (5.1 mL) and cooled to 0° C. Pyridine (0.67 mL, 8.27 mmol, 12 equiv) was added followed by TFA (0.37 mL, 4.82 mmol, 7 equiv). After 30 minutes, TFAA (0.68 mL, 4.82 mmol, 7 equiv) was added. The resulting mixture was allowed to warm to 15° C. and stirred for 20 h. The reaction was diluted with toluene, washed with sodium bicarbonate, dried (MgSO$_4$), and concentrated. The yellow residue was purified via flash chromatography on silica gel column (ethyl acetate/hexanes) to yield of 8-chloro-3-((3aS, 4S,6aR)-2,2-dimethyl-6-(trityloxymethyl)-4,6a-dihydro-3aH-cyclopenta[d][1,3]dioxol-4-yl)imidazo[1,2-a]pyrazine (1-8) as an off-white solid. $^1$H NMR (500 MHz, CDCl$_3$) δ 7.93 (d, 1H, J=3 Hz), 7.64 (d, 1H, J=3 Hz), 7.21-7.49 (m, 15H), 5.94 (br s, 2H), 5.06 (d, 1H, J=5.5 Hz), 4.98 (d, 1H, J=5.5 Hz), 4.45 (m, 2H), 3.89 (d, 1H, J=14.5 Hz), 3.76 (m, 1H), 3.71 (d, 1H, J=14.5 Hz), 1.36 (s, 3H), 1.33 (s, 3H). LRMS m/z (M+H) 563.9 found, 564.2 required.

3-((3aS,4S,6aR)-2,2-dimethyl-6-(trityloxymethyl)-4,6a-dihydro-3aH-cyclopenta[d][1,3]dioxol-4-yl)imidazo[1,2-a]pyrazin-8-amine (1-9)

Liquid ammonia (10 mL) was added to 8-chloro-3-((3aS, 4S,6aR)-2,2-dimethyl-6-(trityloxymethyl)-4,6a-dihydro-3aH-cyclopenta[d][1,3]dioxol-4-yl)imidazo[1,2-a]pyrazine (1-8) (180 mg, 0.32 mmol, 1 equiv) in isopropanol (10 mL). The resulting solution was placed in a high pressure vessel and heated to 100° C. (pressure did not exceed 600 psi) for 20 h. The resulting amber solution was concentrated, and the residue was purified via reverse phase HPLC (H$_2$O/CH$_3$CN gradient w/0.1% TFA present) to afford 3-((3aS,4S,6aR)-2, 2-dimethyl-6-(trityloxymethyl)-4,6a-dihydro-3aH-cyclopenta[d][1,3]dioxol-4-yl)imidazo[1,2-a]pyrazin-8-amine (1-9) as a white solid. $^1$H NMR (500 MHz, CDCl$_3$) δ 7.7 (d, 1H, J=5.5 Hz), 7.21-7.50 (m, 17H), 6.06 (s, 1H), 5.19 (d, 1H, J=5.5 Hz), 4.66 (d, 1H, J=5.5 Hz), 4.33 (m, 1H), 3.91 (d, 1H, J=14 Hz), 3.83 (d, 1H, J=14 Hz), 1.43 (s, 3H), 1.33 (s, 3H). LRMS m/z (M+H) 544.9 found, 545.2 required.

(1S,2R,5S)-5-(8-aminoimidazo[1,2-a]pyrazin-3-yl)-3-(hydroxymethyl)cyclopent-3-ene-1,2-diol (1-10)

Concentrated HCl solution (0.6 mL) was added to 3-((3aS, 4S,6aR)-2,2-dimethyl-6-(trityloxymethyl)-4,6a-dihydro-3aH-cyclopenta[d][1,3]dioxol-4-yl)imidazo[1,2-a]pyrazin-8-amine (1-9) (130 mg, 0.239 mmol, 1 equiv) in methanol (3 mL) and heated to 65° C. After 2 hours the mixture was cooled to 23° C. C and purified via reverse phase HPLC (H$_2$O/CH$_3$CN gradient w/0.1% TFA present) to afford (1S,2R,5S)-5-(8-aminoimidazo[1,2-a]pyrazin-3-yl)-3-(hydroxymethyl)cyclopent-3-ene-1,2-diol (1-10) as an amber solid. $^1$H NMR (500 MHz, CD$_3$OD) δ 8.04 (d, 1H, J=5.5 Hz), 7.62 (s, 1H), 7.24 (d, 1H, J=5.5 Hz), 5.93 (s, 1H), 4.51 (d, 1H, J=5.5 Hz), 4.31 (m, 2H), 4.23 (br m, 1H), 4.10 (t, 1H, J=5.5 Hz). LRMS m/z (M+H) 263.1 found, 263.1 required.

EXAMPLE 2
(1R,2S,3S)-3-(8-aminoimidazo[1,2-a]pyrazin-3-yl)cyclopentane-1,2-diol
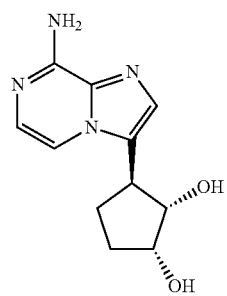
(I)
SYNTHETIC SCHEME
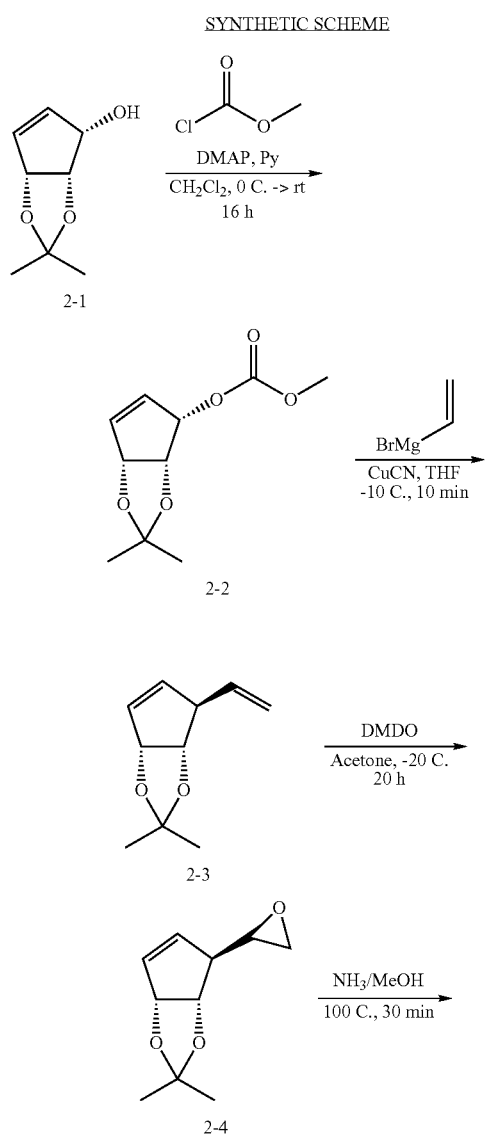
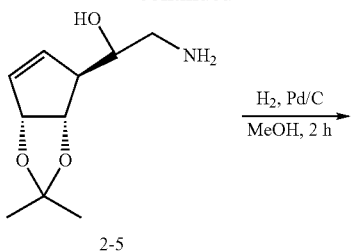
2-5
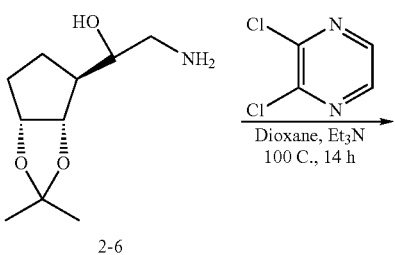
2-6
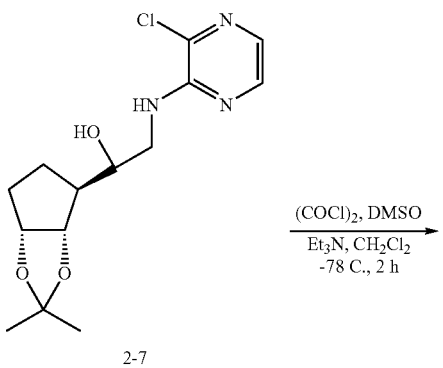
2-7
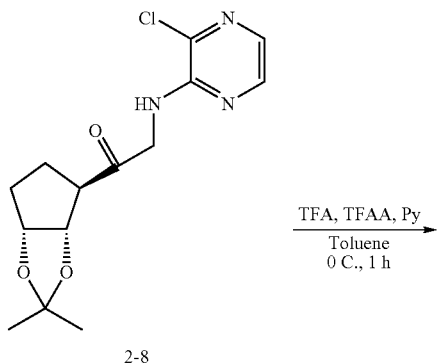
2-8
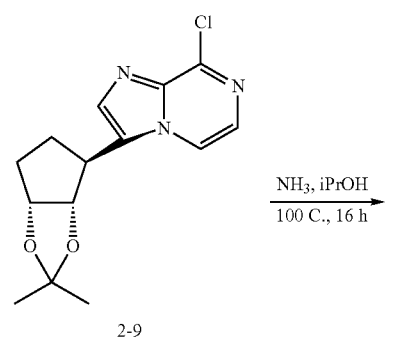
2-9

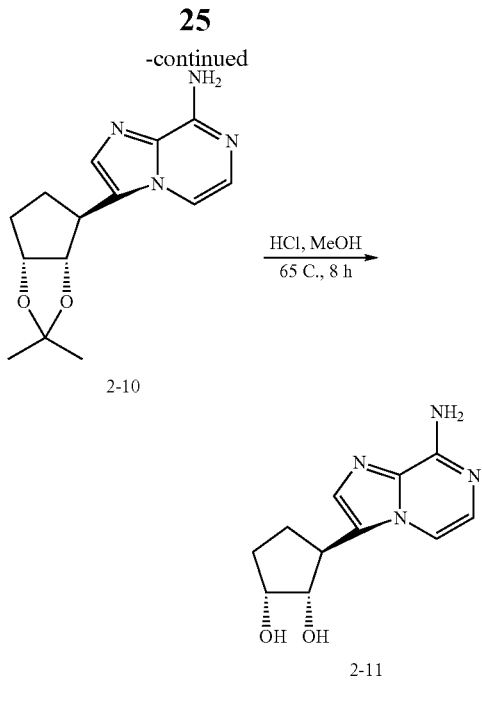

5.84-5.73 (m, 2H); 5.17 (d, J=5.7 Hz, 1H); 5.10-5.00 (m, 2H); 4.45 (d, J=5.7 Hz, 1H); 3.45 (d, J=7.3 Hz, 1H); 1.43 (s, 3H); 1.34 (s, 3H).

(3aS,4S,6aR)-2,2-dimethyl-4-((S)-oxiran-2-yl)-4,6a-dihydro-3aH-cyclopenta[d][1,3]dioxole (2-4)

(3aS,4R,6aR)-2,2-dimethyl-6-(trityloxymethyl)-4-vinyl-4,6a-dihydro-3aH-cyclopenta[d][1,3]dioxole (2-3) (7.0 g, 42.1 mmol, 1.0 equiv) was dissolved in a freshly prepared solution of DMDO in acetone (460 mL, 0.085 M, 0.9 equity), stirred at −20° C. for 7 hours and stored at −18° C. overnight. The reaction mixture was concentrated and purified via flash chromatography on a silica gel column (ethyl acetate/hexanes) to yield desired (3aS,4S,6aR)-2,2-dimethyl-4-((S)-oxiran-2-yl)-4,6a-dihydro-3aH-cyclopenta[d][1,3]dioxole (2-4) as a colorless oil. $^1$H NMR (500 MHz, CDCl$_3$): δ 5.92 (t, J=5.7 Hz, 1H); 5.75-5.71 (m, 1H); 5.17 (d, J=5.8 Hz, 1H); 4.70-4.57 (m, 1H); 2.98-2.89 (m, 2H); 2.77-2.72 (m, 1H); 2.55 (dt, J=4.8, 2.8 Hz, 1H); 1.41 (s, 3H); 1.35 (d, J=2.3 Hz, 3H).

(3aR,4S,6aR)-2,2-dimethyl-4,6a-dihydro-3aH-cyclopenta[d][1,3]dioxol-4-yl methyl carbonate (2-2)

(3aS,4S,6aR)-2,2-dimethyl-4,6a-dihydro-3aH-cyclopenta[d][1,3]dioxol-4-ol (2-1) (9.76 g, 62.5 mmol, 1.0 equiv) was dissolved in DCM (200 mL). Pyridine (7.58 mL, 94.0 mmol, 1.5 equiv) was added and the mixture stirred at 0° C. After 1 hour DMAP (3.05 g, 25.0 mmol, 0.4 equiv) was added followed by methyl chloroformate (19.4 mL, 250 mmol, 4 equiv). The resulting mixture was stirred overnight, and the temperature was allowed to slowly increase to room temperature. The reaction was partitioned between DCM and water, and the organic layer was separated and washed with water, dried (MgSO$_4$), and concentrated to yield desired (3aR,4S,6aR)-2,2-dimethyl-4,6a-dihydro-3aH-cyclopenta[d][1,3]dioxol-4-yl methyl carbonate (2-2) as a colorless oil. $^1$H NMR (500 MHz, CDCl$_3$): δ 6.10 (d, J=5.9 Hz, 1H); 5.91 (d, J=5.9 Hz, 1H); 5.30 (d, J=5.4 Hz, 1H); 5.03 (d, J=5.7 Hz, 1H); 4.92 (t, J=5.5 Hz, 1H); 3.83 (s, 3H); 1.40 (s, 3H); 1.38 (s, 3H).

(3aS,4R,6aR)-2,2-dimethyl-6-(trityloxymethyl)-4-vinyl-4,6a-dihydro-3aH-cyclopenta[d][1,3]dioxole (2-3)

(3aR,4S,6aR)-2,2-dimethyl-4,6a-dihydro-3aH-cyclopenta[d][1,3]dioxol-4-yl methyl carbonate (2-2) (10.4 g, 48.4 mmol, 1 equiv) was dissolved in anhydrous THF (242 mL) and cooled to −10° C. To the resulting mixture was added copper(I) cyanide (1.30, 14.5 mmol, 0.30 equiv) followed by 0.7 M vinylmagnesium bromide solution in THF (173 mL, 121 mmol, 2.5 equiv). Reaction was complete after 10 minutes, as indicated by TLC. The reaction was quenched with NH$_4$Cl (100 mL) and extracted with Et$_2$O (3×150 mL). The combined organic extracts were washed with brine, dried (MgSO$_4$), and concentrated. Purification via flash chromatography on silica gel column (ethyl acetate/hexanes) gave (3aS,4R,6aR)-2,2-dimethyl-6-(trityloxymethyl)-4-vinyl-4,6a-dihydro-3aH-cyclopenta[d][1,3]dioxole as a colorless oil, $^1$H NMR (500 MHz, CDCl$_3$): δ 5.86 (d, J=5.8 Hz, 1H);

(S)-2-amino-1-((3aS,4S,6aR)-2,2-dimethyl-4,6a-dihydro-3aH-cyclopenta[d][1,3]dioxol-4-yl)ethanol (2-5)

(3aS,4S,6aR)-2,2-dimethyl-4-((S)-oxiran-2-yl)-4,6a-dihydro-3aH-cyclopenta[d][1,3]dioxole (2-4) (3 g, 16.5 mmol, 1.0 equiv) was dissolved in a solution of ammonia in methanol (200 mL, 7 N). The mixture was heated in the microwave at 100° C. for 30 minutes. The reaction was concentrated to afford desired (S)-2-amino-1-((3aS,4S,6aR)-2,2-dimethyl-4,6a-dihydro-3aH-cyclopenta[d][1,3]dioxol-4-yl)ethanol (2-5) as an amber oil that was carried to the next step without further purification. $^1$NMR (500 MHz, CDCl$_3$): δ 5.98-5.86 (m, 1H); 5.91-5.65 (m, 1H); 5.13 (s, 1H); 4.80-4.45 (m, 1H); 3.03 (s, 1H); 2.95-2.83 (m, 2H); 2.74 (s, 2H); 2.61 (s, 2H); 1.41 (s, 3H); 1.35 (s, 3H).

(S)-2-amino-1-((3aS,4S,6aR)-2,2-d methyltetrahydro-3aH-cyclopenta[d][1,3]dioxol-4-yl)ethanol (2-6)

(S)-2-amino-1-((3aS,4S,6aR)-2,2-dimethyl-4,6a-dihydro-3aH-cyclopenta[d][1,3]dioxol-4-yl)ethanol (2-5) (3.22 g, 16.2 mmol, 1.0 equiv) was dissolved in MeOH (150 mL) and 10% Pd/C (1.72 g, 16.2 mmol, 1.0 equiv) was carefully added. The resulting mixture stirred for 2 hours under a H$_2$ atmosphere. The reaction mixture was filtered through a plug of celite, and the solids were washed with MeOH (4×50 mL). The filtrate was concentrated to afford desired (S)-2-amino-1-((3aS,4S,6aR)-2,2-dimethyltetrahydro-3aH-cyclopenta[d][1,3]dioxol-4-yl)ethanol (2-6) as a colorless oil. $^1$H NMR (500 MHz, CDCl$_3$): δ 4.65 (s, 1H); 4.35 (s, 1H); 3.67 (s, 2H); 3.50 (s, 1H); 3.04 (t, J=7.3 Hz, 1H); 2.91 (d, J=27.3 Hz, 1H); 2.70 (d, J=11.1 Hz, 1H); 2.26-2.21 (m, 1H); 1.96 (d, J=14.6 Hz, 2H); 1.89 (d, J=20.3 Hz, 1H); 1.77 (s, 1H); 1.52-1.41 (m, 3H); 1.35-1.26 (m, 3H).

(S)-2-(3-chloropyrazin-2-ylamino)-1-((3aS,4S,6aR)-2,2-dimethyltetrahydro-3aH-cyclopenta[d][1,3]dioxol-4-yl)ethanol (2-7)

(S)-2-amino-1-((3aS,4S,6aR)-2,2-dimethyltetrahydro-3aH-cyclopenta[d][1,3]dioxol-4-yl)ethanol (2-6) (3.22 g, 15.0 mmol, 1.0 eq) was dissolved in dioxane (150 mL). 2,3-Dichloropyrazine (4.46 g, 29.9 mmol, 2 equiv) was added followed by triethylamine (8.34 mL, 59.8 mmol, 4 equiv) and the reaction mixture was heated to reflux overnight. Concentration and purification via flash chromatography on a silica gel column (ethyl acetate/hexanes) yielded desired (S)-2-(3-chloropyrazin-2-ylamino)-1-((3aS,4S,6aR)-2,2-dimethyltetrahydro-3aH-cyclopenta[d][1,3]dioxol-4-yl)ethanol (2-7) as a colorless oil. $^1$H NMR (500 MHz, CDCl$_3$): δ 7.88 (dd, J=5.5, 2.7 Hz, 1H); 7.60 (d, J=2.7 Hz, 1H); 5.74 (d, J=31.9 Hz, 1H); 4.68-4.63 (m, 1H); 4.34 (t, J=5.4 Hz, 1H); 3.88 (ddd, J=14.5, 6.7, 2.5 Hz, 1H); 3.81-3.69 (m, 2H); 3.63-3.46 (m, 2H); 2.15-2.04 (m, 1H); 2.03-1.88 (m, 1H); 1.83-1.72 (m, 1H); 1.69-1.52 (m, 1H); 1.50 (d, J=13.2 Hz, 3H); 1.32 (d, J=4.5 Hz, 3H). LRMS m/z (M+H) 313.9 found, 314.1 required.

2-(3-chloropyrazin-2-ylamino)-1-((3aS,4R,6aR)-2,2-dimethyltetrahydro-3aH-cyclopenta[d][1,3]dioxol-4-yl)ethanone (2-8)

Oxalyl chloride (2.75 mL, 31.6 mmol, 3.0 equiv) in DCM (35 mL) was added dropwise to DMSO (3.00 mL, 42.1 mmol, 4.0 equiv) in DCM (35 mL) at −78° C. After 30 minutes, (S)-2-(3-chloropyrazin-2-ylamino)-1-((3aS,4S,6aR)-2,2-dimethyltetrahydro-3aH-cyclo-penta[d][1,3]dioxol-4-yl)ethanol (2-7) (3.30 g, 10.5 mmol, 1 equiv) in DCM (35 mL) was added dropwise. The resulting mixture was stirred at −78° C. for 1 hour, at which point triethylamine (6.60 mL, 47.3 mmol, 4.5 equiv) was added. The cooling bath was removed, and after 30 minutes the reaction mixture was concentrated. The resulting yellow residue was purified via flash chromatography on a silica gel column (ethyl acetate/hexanes) to yield 2-(3-chloropyrazin-2-ylamino)-1-((3aS,4R,6aR)-2,2-dimethyltetrahydro-3aH-cyclopenta[d][1,3]-dioxol-4-yl)ethanone (2-8) as a yellow solid. $^1$H NMR (500 MHz, CDCl$_3$): δ 7.92 (d, J=2.7 Hz, 1H); 7.63 (d, J=2.7 Hz, 1H); 5.93 (s, 1H); 4.80 (d, J=5.7 Hz, 1H); 4.73 (t, J=5.4 Hz, 1H); 4.47 (dd, J=19.7, 5.0 Hz, 1H); 4.31 (dd, J=19.7, 4.7 Hz, 1H); 3.17 (d, J=8.1 Hz, 1H); 2.25-2.17 (m, 1H); 1.93-1.84 (m, 2H); 1.78-1.68 (m, 1H); 1.47 (s, 3H); 1.32 (s, 3H). LRMS m/z (M+H) 312.0 found, 312.1 required.

8-chloro-3-((3aS,4S,6aR)-2,2-dimethyltetrahydro-3aH-cyclopenta[d][1,3]dioxol-4-yl)imidazo[1,2-a]pyrazine (2-9)

2-(3-chloropyrazin-2-ylamino)-1-((3aS,4R,6aR)-2,2-dimethyltetrahydro-3aH-cyclopenta[d][1,3]dioxol-4-yl)ethanone (2-8) (1.2 g, 3.85 mmol, 1 equiv) was dissolved in toluene (28 mL) and the mixture was cooled to 0° C. Pyridine (3.74 mL, 46.2 mmol, 12 equiv) was added followed by TFA (2.08 mL, 26.9 mmol, 7 equiv). After 30 minutes, TFAA (3.81 mL, 26.9 mmol, 7 equiv) was added. The resulting mixture was stirred for 1 h, then was concentrated and the yellow residue was purified via flash chromatography on a silica gel column (ethyl acetate/hexanes) to yield desired 8-chloro-3-((3aS,4S,6aR)-2,2-dimethyltetrahydro-3aH-cyclopenta[d][1,3]dioxol-4-yl)imidazo[1,2-a]pyrazine (2-9) as a white solid. $^1$H NMR (500 MHz, CDCl$_3$): δ 8.19 (d, J=4.6 Hz, 1H); 7.84 (d, J=4.6 Hz, 1H); 7.67 (s, 1H); 4.81 (d, J=5.2 Hz, 1H); 4.57 (dd, J=6.0, 2.6 Hz, 1H); 3.47 (s, 1H); 2.52-2.41 (m, 1H); 2.09-2.05 (m, 3H); 1.58 (s, 3H); 1.34 (s, 3H). LRMS m/z (M+H) 293.9 found, 294.1 required.

3-((3aS,4S,6aR)-2,2-dimethyltetrahydro-3aH-cyclopenta[d][1,3]dioxol-4-yl)imidazo[1,2-a]pyrazin-8-amine (2-10)

Liquid ammonia (50 mL) was added to 8-chloro-3-((3aS,4S,6aR)-2,2-dimethyltetrahydro-3aH-cyclopenta[d][1,3]dioxol-4-yl)imidazo[1,2-a]pyrazine (2-9) (1.5 g, 5.1 mmol, 1 equiv) in isopropanol (50 mL). The resulting solution was placed in a high pressure vessel and heated to 100° C. After 16 hours, no more starting material was present, the amber solution was concentrated to afford desired 3-((3aS,4S,6aR)-2,2-dimethyltetrahydro-3aH-cyclopenta[d][1,3]dioxol-4-yl)imidazo[1,2-a]pyrazin-8-amine (2-10) as a tan solid that was carried to the next step without further purification. $^1$H NMR (500 MHz, CDCl$_2$): δ 7.50 (d, J=4.7 Hz, 1H); 7.36 (t, J=4.6 Hz, 1H); 7.23 (s, 1H); 5.60 (s, 2H); 4.78 (s, 1H); 4.64 (d, J=5.7 Hz, 1H); 3.44 (d, J=6.9 Hz, 1H); 2.43-2.33 (m, 1H); 2.04-1.93 (m, 3H); 1.55 (s, 3H); 1.34 (s, 3H). LRMS m/z (M+H) 275.0 found, 275.1 required.

(1R,2S,3S)-3-(8-aminoimidazo[1,2-a]pyrazin-3-yl)cyclopentane-1,2-diol (2-11)

Concentrated HCl (4 mL) was added to 3-((3aS,4S,6aR)-2,2-dimethyltetrahydro-3aH-cyclopenta[d][1,3]dioxol-4-yl)imidazo[1,2-a]pyrazin-8-amine (2-10) (1.20 g, 4.37 mmol, 1 equiv) in methanol (20 mL) and the mixture was heated to 65° C. After 8 hours, no more starting material was present and the mixture was concentrated to afford desired (1R,2S,3S)-3-(8-aminoimidazo[1,2-a]pyrazin-3-yl)cyclopentane-1,2-diol (2-11) as a tan solid. $^1$H NMR (500 MHz, CD$_3$OD): δ 8.06 (d, J=5.8 Hz, 1H); 7.82 (s, 1H); 7.27 (d, J=5.7 Hz, 1H); 4.14 (s, 1H); 4.04 (dd, J=9.3, 4.5 Hz, 1H); 3.55 (q, J=9.1 Hz, 1H); 2.40-2.29 (m, 1H); 2.22-2.10 (m, 1H); 1.92-1.80 (m, 2H). LRMS m/z (M+H) 235.1 found, 235.1 required.

In vitro AHCY Activity Assay

The AHCY activity of the compounds of the invention can be measured by the following in vitro assay.

The AHCY enzyme assay is based on the principle of fluorescence emission following incubation of a reactive dye with the products of an AHCY catalyzed reaction. The reactive dye (Thioglo1) binds homocysteine through its thiol-containing moiety. The products of the AHCY catalyzed reaction, adenosine and homocysteine, are produced from the hydrolysis of SAH (s-adenosylhomocysteine) through AHCY's hydrolase activity.

The reaction is optimized in 96-, 384-, 1536- and 3456-assay plate formats with recombinant expressed human or mouse AHCY enzyme. When run under initial velocity conditions, the assay is suitable for IC50 and % inhibition calculations.

Materials:
1) ThioGlo1 (catalog 595501, Calbiochem); 100 mM in DMSO
2) SAH (catalog A-9384, Sigma); 4.69 mM with 0.06 N HCl
3) Aristeromycin (catalog A-0928, Sigma); 100 mM in DMSO
4) NAD (catalog 43410, Sigma); 14.5 mM in water
5) EDTA in 500 mM pH 8 (catalog BP2482-100, Fisher)
6) DTT stock 200 mM in water
7) AHCY enzyme (diluted with 100 mM tris pH7.5)

Dilutions immediately prior to use:
1. SAH 750 µM (10×) (dilute with 100 mM Iris pH 7.5)
2. Aristeromycin (10×) (dilute to 1 mM with 100 mM Tris pH7.5)
3. ThioGlo1 (10×) (dilute to 100 µM in Tris pH7.5)
4. AHCY assay buffer (3.3×): 3 µM DTT, 150 µM NAD, 3 mM EDTA Protocol: As per 96-assay plate well
1. Add 5 µL AHCY enzyme [30 ng/ul in 100 mM Tris pH7.5]
2. Add 5 µL DMSO or inhibitor
3. Add 15 µL AHCY assay buffer
4. Add 15 µL 100 mM Tris pH 7.5

5. Incubate 37° C. 30 min
6. Add 5 μL 750 uM SAH
7. Incubate 37° C. 10 min
8. Add 5 μl 100 μM ThioGlo1
9. Incubate 37° C. 15 mins
10. Read plate (Ex 380 Em 510)

Example 1 was tested according to this protocol (n=4) and gave an $IC_{50}$=4 nM. Example 2 was tested according to this protocol (n=2) and gave an $IC_{50}$=692 nM. These values attest to the properties of these compounds as potent inhibitors of the enzyme AHCY.

Cell-Based Assay of AHCY Inhibition

The AHCY activity of the compounds of the invention can be measured by the following cell-based assay.

This assay measures secreted homocysteine over a period of time from adherent HEK293 and/or SH-SY5Y cells as a measure of the ability of a compound to enter a cell in culture and effectively inhibit AHCY in the context of the cellular milieu. Post treatment collection of the adherent Hek293 and/or SH-SY5Y cells is also made for a viability and proliferation measure. Since the amount of secreted homocysteine is limited by the amount of SAH that is converted to homocysteine in the cells and its subsequent secretion, an EC50 measure and % inhibition relative to DMSO control cells can be made. Since the amount of secreted metabolites such as homocysteine can also be related to the absolute and cellular viability, an MTT (3-(4,5-Dimethylthiazol-2-yl)-2,5-diphenyltetrazolium bromide) measure of proliferation and relative cytotoxicty (as compared to control conditions) may also be made.

Protocol:
1. The day before compound treatment, plate 20,000 cells (Hek293 or SH-SY5Y) in 96 well cell culture treated plates in 100 μl of cell culture media (DMEM and 10% fetal bovine serum).
2. Add fresh media plus compound (and DMSO treated controls) for 72 hrs.
3. Collect conditioned media for measurement of secreted homocysteine and perform viability/proliferation assay on adherent cells.

Measure of Secreted Homocysteine:
1. Add 25 μl conditioned media, standard or control in 96-well assay plate
2. Add 25 μl internal standard
3. Add 10 μl reduction solution
4. Add 50 μl derivatisation reagent
5. Incubate for 10 min in PCR (polymerase chain reaction) machine at 60° C., stop reaction at 4° C. or on ice.
6. Add 50 μl precipitating solution
7. Mix well, incubate for 10 min at 4° C. and centrifuge for 10 min at 2,000×
8. Inject 20 μl of the supernatant into HPLC system.
   a. Chromatographic conditions:
      i. Column material: Imtakt Unisom C18, 3 μm
      ii. Column dimension: 50 mm×4.6 mm
      iii. Flow rate: 1.5 ml/min
      iv. Detection: Fluorescence: Excitation 385 nm, Emission 515 nm
      v. Injection volume: 20 μl
      vi. Running time: 3.5 min
   b. Calculation:

(peak height patient*concentration of the calibrator/peak height internal standard patient)
*$F$=concentration patient sample ($F$=IS peak of calibrator/$Hcy$ peak of calibrator)

Measure of Cell Viability/Proliferation:
1. Add mixture of 10 μl 5 mg/ml MTT labeling reagent plus 90 μl fresh assay media to cells.
2. Incubate for 4 hrs at 37° C. in cell culture incubator
3. Add 100 μl of solubilization solution.
4. Incubate for 16 hrs at 37° C. in cell culture incubator
5. ReaDMEMd absorbance at 550 nM and 690 nM.
6. Express readout as 550 nM-690 nM.

Example 1 was tested according to this protocol (n=2) and gave an $IC_{50}$=4 nM. Example 2 was tested according to this protocol (n=2) and gave an $IC_{50}$=1.4 nM. These values attest to the properties of these compounds as potent inhibitors of AHCY in a cell-based format and their ability to lower homocysteine concentration intracellularly.

The following abbreviations are used throughout the text:
AdoHcy S-Adenosyl homocysteine
Me: methyl
Et: ethyl
t-Bu: tent-butyl
i-Pr: isopropyl
Ph: phenyl
DCM: dichloromethane
THF: tetrahydrofuran
Ac: acetyl
DMAP: 4-Dimethylaminopyridine
DMDO: dimethyldioxirane
NAD: nicotinamide adenine dinucleotide
DMEM: Dulbecco's modified Eagle's medium
MTT: 3-(4,5-Dimethylthiazol-2-yl)-2,5-diphenyltetrazolium bromide
PCR: polymerase chain reaction
DMSO: dimethylsulfoxide
TFA: trifluoroacetic acid
TFAA: trifluoroacetic acid anhydride
Tr triphenylmethyl
rt: room temperature
aq: aqueous
HPLC: high performance liquid chromatography
MS: mass spectrometry
$CDCl_3$: chloroform-d
CuCN: copper(I) cyanide
DIPEA: diisopropylethylamine
DMF: N,N-dimethylformamide
$Et_2O$: diethylether
LRMS: low resolution mass spectrum
MeOH: methanol
$MgSO_4$: magnesium sulfate
NMR: nuclear magnetic resonance
Py: pyridine While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

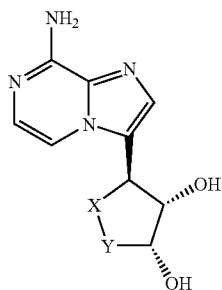

or a pharmaceutically acceptable salt thereof, wherein
X—Y is selected from the group consisting of
(1) $CH_2$—$CR^1R^2$,
(2) $CH$=$CR^1$;
$R^1$ is selected from the group consisting of
(1) hydrogen,
(2) hydroxy,
(3) —$C_{1-6}$ alkyl, wherein said alkyl is optionally substituted with
(a) halogen, or
(b) hydroxy; and
$R^2$ is selected from the group consisting of
(1) hydrogen,
(2) hydroxy,
(3) —$C_{1-6}$ alkyl, wherein said alkyl is optionally substituted with
(a) halogen, or
(b) hydroxy.

2. The compound of claim 1, or a pharmaceutically acceptable salt thereof, wherein X—Y is $CH_2$—$CR^1R^2$, and $R^1$ is selected from the group consisting of
(1) hydrogen, and
(2) —$C_{1-3}$ alkyl, wherein said alkyl is optionally substituted with
(a) halogen, or
(b) hydroxy.

3. The compound of claim 2, or a pharmaceutically acceptable salt thereof, wherein X—Y is $CH_2$—$CR^1R^2$, and $R^1$ is selected from the group consisting of
(1) hydrogen, and
(2) —$CH_2OH$.

4. The A compound of claim 1, or a pharmaceutically acceptable salt thereof, wherein X—Y is $CH$=$CR^1$, and $R^1$ is selected from the group consisting of
(1) hydrogen, and
(2) —$C_{1-3}$ alkyl, wherein said alkyl is optionally substituted with
(a) halogen, or
(b) hydroxy.

5. The compound of claim 1, or a pharmaceutically acceptable salt thereof, wherein $CH$=$CR^1$, and $R^1$ is selected from the group consisting of
(1) hydrogen, and
(2) —$CH_2OH$.

6. The compound of claim 1, which is selected from the group consisting of

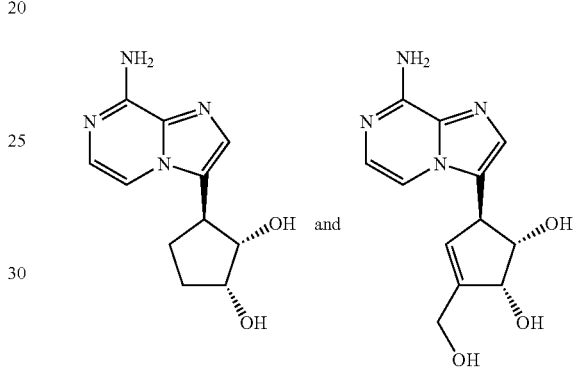

or a pharmaceutically acceptable salt thereof.

7. The pharmaceutical composition comprising a compound of any of claims 1-6 or a pharmaceutically acceptable salt thereof, and a pharmaceutically acceptable carrier.

* * * * *